(12) United States Patent
Koch

(10) Patent No.: US 6,429,410 B1
(45) Date of Patent: Aug. 6, 2002

(54) CIRCUIT FOR HEATING A COMPONENT

(75) Inventor: Stefan Koch, Achern (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/341,370

(22) PCT Filed: Nov. 6, 1998

(86) PCT No.: PCT/DE98/03240

§ 371 (c)(1),
(2), (4) Date: Sep. 30, 1999

(87) PCT Pub. No.: WO99/24887

PCT Pub. Date: May 20, 1999

(30) Foreign Application Priority Data

Nov. 8, 1997 (DE) .......................... 197 49 535

(51) Int. Cl.⁷ ................................ H05B 1/02
(52) U.S. Cl. ................... 219/497; 219/506; 219/492; 219/499; 236/15 A
(58) Field of Search ................. 219/481, 492, 219/497, 499, 501, 505, 508; 307/117; 236/15 A, 15 BG; 374/101–104

(56) References Cited

U.S. PATENT DOCUMENTS

| 4,049,044 A | * | 9/1977 | Cohen ..................... 236/94 |
| 4,438,323 A | * | 3/1984 | Milnes ..................... 219/243 |
| 4,573,058 A | * | 2/1986 | Brooks ..................... 219/216 |
| 4,684,959 A | * | 8/1987 | Mori et al. ................ 400/120 |
| 4,686,352 A | * | 8/1987 | Nawrot et al. ............. 219/250 |
| 4,818,313 A | * | 4/1989 | Sundberg .................. 219/492 |
| 5,656,190 A |   | 8/1997 | Aoki |

FOREIGN PATENT DOCUMENTS

| DE | 43 12 289 | 10/1994 |
| DE | 195 31 786 | 3/1997 |
| EP | 0 779 426 | 6/1997 |

* cited by examiner

Primary Examiner—Mark Paschall
(74) Attorney, Agent, or Firm—Kenyon & Kenyon

(57) ABSTRACT

A circuit for heating a component is maintained at a predefined operating temperature by a resistance heating element. A control system for the temperature of the resistance heating element is provided. From a determination of the average electrical energy delivered to the resistance heating element, an analysis arrangement concludes that the predefined operating temperature of the component to be heated has been at least approximately reached.

18 Claims, 1 Drawing Sheet

CIRCUIT FOR HEATING A COMPONENT

FIELD OF THE INVENTION

The present invention relates to a circuit for heating a component.

BACKGROUND INFORMATION

German Patent No. 195 31 786 describes a circuit arrangement for activating a heating resistor that is provided, in particular, for heating an air quality sensor. The temperature of the heating resistor is regulated to a predefined value. The heating resistor is activated with a two-position temperature controller. If the reference temperature and actual temperature differ from one another, current flow through the heating resistor then occurs. The actual temperature of the heating resistor is determined indirectly by sensing its electrical resistance. The heating resistor is a constituent of a voltage divider through which, during the switched-off phase of the heating current, there flows a small current that allows a conclusion to be drawn, via the voltage drops in the voltage divider, as to the internal resistance of the heating element.

Another circuit arrangement for temperature regulation of a resistance heating system has been described in German Patent No. 43 12 289. With this conventional circuit arrangement, continuous closed-loop control of the heating output is provided instead of a two-position control system. Here again, the electrical resistance of the resistance heating element, which is arranged in a voltage divider, is sensed. The difference between the voltage drops occurring, on the one hand, at a known resistance and, on the other hand, at the resistance heating element is evaluated. The magnitude of the difference defines the operating voltage of the voltage divider containing the resistance heating element.

The known resistance heating elements are provided for heating of sensors which must be at an operating temperature higher than ambient temperature in order to work correctly. In the case of the conventional circuit arrangements, it is assumed that the operating temperature of the sensor always corresponds at least approximately to that of the resistance heating element.

It is an object of the present invention to describe a circuit for heating a component which indicates, with simple means, the fact that the operating temperature of the component to be heated has been reached.

SUMMARY OF THE INVENTION

A temperature of the component to be heated is not necessary. The fact that an operating temperature has been reached is deduced exclusively from the operating behavior of the resistance heating element. According to the present invention, at least one observation time interval is defined, within which a determination of the average energy delivered to the resistance heating element is provided. The fact that the average energy falls below a predefined threshold is interpreted as meaning that the predefined operating temperature of the component to be heated has at least approximately been reached. The present invention makes use of the fact that the energy to be delivered to the heating element during the operation of heating up the component to be heated is higher than in the steady state operating condition, in which the component to be heated has reached the operating temperature.

The average energy threshold to be ascertained is preferably determined experimentally. In the context of series production, an individual definition of the threshold for each component to be heated can be performed at the end of the line.

It is particularly advantageous to use a two-position controller for temperature regulation of the resistance heating element. The two-position temperature controller compares the actual temperature occurring at the resistance heating element to the predefined reference temperature, and, as a function of the result, either connects the resistance heating element to an energy source or interrupts the connection.

An advantageous development of this embodiment according to the present invention provides for the switched-on time of the two-position temperature controller within the observation time interval to be determined. The switched-on time is a direct indication of the average energy delivered to the resistance heating element. Instead of an integration of the energy delivered to the resistance heating element, all that is to be provided is thus a determination of a duration. What is to be defined in this case as the threshold of the average energy is a maximum duration within the observation time interval.

Another advantageous development of this embodiment according to the present invention provides for the number of switch-on events of the two-position temperature controller within the observation time interval to be determined. Once the component to be heated has been heated up, the two-position temperature controller reduces the average electrical energy delivered to the resistance heating element by switching on and off more frequently. In this case, the minimum threshold for the average energy corresponds to the definition of a number of switch-on events which must at least be attained within the observation time interval.

Another advantageous embodiment of the circuit according to the present invention provides for the internal resistance of the resistance heating element to be evaluated as an indication of its temperature. As a result, a separate temperature sensor for sensing the temperature of the resistance heating element is not necessary. The internal resistance of the resistance heating element can be determined using one of the actions explained in the documents cited in the "Background Information" section.

A sensor is preferably provided as the component to be heated. The sensor can be, for example, a gas sensor which converts the constituents of a gas being investigated into a corresponding output signal. Sensors of this kind are used, for example, in determining the gas constituents of internal combustion engine exhaust gases, or ascertaining the quality of inhaled air by evaluating at least the CO concentration and NOx concentration in the inhaled air.

DETAILED DESCRIPTION

Figure 1:
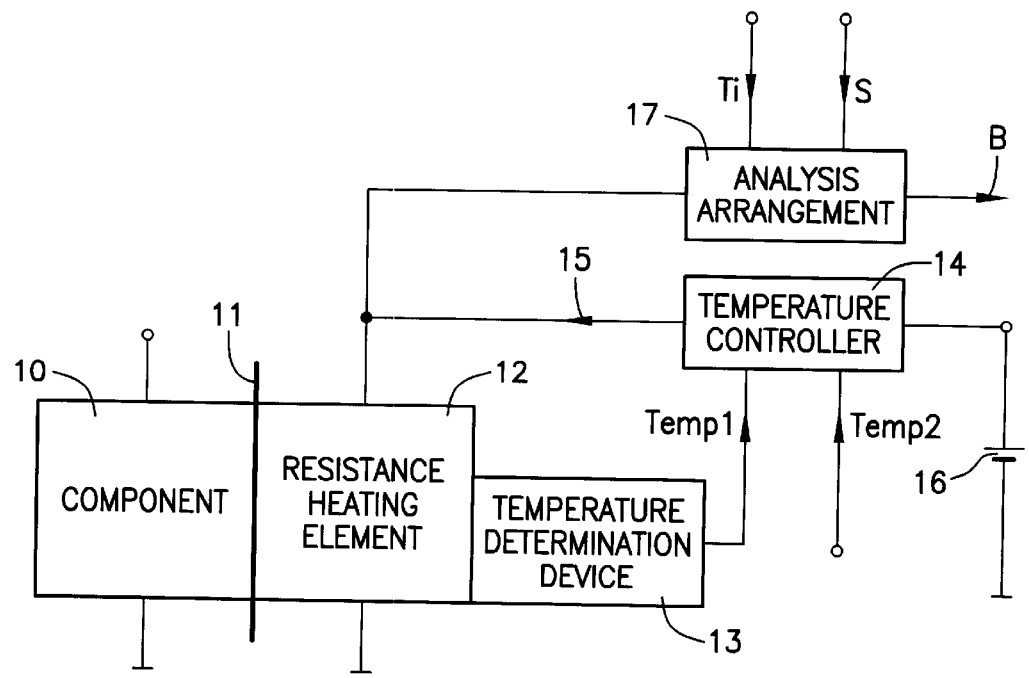
FIG. 1 shows a block diagram of a circuit according to the present invention for heating a component.

FIG. 1 shows a component 10 to be heated, which is thermally connected via a thermal coupling 11 to a resistance heating element 12. The temperature of the resistance heating element is determined by a temperature determination device 13, and conveyed to a temperature controller 14 as actual temperature Temp1. Temperature controller 14 also has delivered to it the reference temperature Temp2 of resistance heating element 12. Temperature controller 14 emits a heating signal 15 to resistance heating element 12. The energy for heating resistance heating element 12 is made available by an energy source 16. Heating signal 15 is conveyed to an analysis arrangement 17 which additionally has conveyed to it an observation time interval Ti and a threshold S. Analysis arrangement 17 emits an operational readiness signal B.

The circuit according to the present invention for heating component 10 operates as follows:

Component 10 to be heated is, for example, a sensor that must be at a predefined operating temperature in order to work correctly. Sensors of this kind are, for example, gas sensors which detect the chemical constituents of a gas and sense their concentrations. Gas sensors are used, for example, to analyze the exhaust gas of internal combustion engines so as to influence fuel metering as a function of the result. Other gas sensors analyze the composition of inhaled air so as to be able to influence a ventilation valve as a function of the result. In chemical sensors of this kind, the temperature of the sensor is generally incorporated directly into the measurement result. A determination of the temperature of this kind of sensor indirectly, for example, by way of its internal electrical resistance, is therefore not sufficiently accurate in all cases. Additional complexity due to the use of a separate temperature probe is undesirable. Provision is therefore made, according to the present invention, for the average energy delivered to resistance heating element 12 within observation time interval Ti to be determined and compared to the predefined threshold S. When threshold S is crossed, operational readiness signal B is issued.

The temperature of resistance heating element 12 is regulated to the predefined reference temperature Temp2 by temperature controller 14. Temperature controller 14 compares reference temperature Temp2 to actual temperature Temp1 of resistance heating element 12. Temperature determination device 13 is provided for determining the temperature of resistance heating element 12, and can be a temperature sensor. Preferably the temperature is determined indirectly via the internal resistance of resistance heating element 12. The internal resistance is a direct indication of the temperature. Determination of the internal resistance of resistance heating element 12 will not be discussed here in more detail; reference is made to the existing art cited initially. German Patent No. 195 31 786 describes a circuit in which resistance heating element 12 is arranged in a voltage divider. From voltage drops at the voltage divider which occur as a result of a rest current during current-flow off periods, conclusions are drawn as to the internal resistance of resistance heating element 12. A circuit in which an interruption in the heating of resistance heating element 12 is not provided is described in German Patent No. 43 12 289. In this, voltage drops are determined while the heating current is flowing, and are utilized for continuous regulation of the operating voltage of resistance heating element 12.

Temperature controller 14 is preferably configured as a two-position temperature controller. The two-position temperature controller compares reference temperature Temp2 to actual temperature Temp1. As long as reference temperature Temp2 is not exceeded, the two-position temperature controller connects energy source 16 to resistance heating element 12. In this case, heating signal 15 is at least approximately equal to the voltage of energy source 16. Heating signal 15 can also, however, be regarded as the current flowing through resistance heating element 12. Instead of the configuration of temperature controller 14 as a two-position controller, it is also possible to provide a continuous control system.

Analysis arrangement 17 determines the average energy delivered to resistance heating element 12 within the predefined observation time interval Ti. According to the exemplary embodiment according to the present invention shown in FIG. 1, this can be accomplished, for example, by analyzing heating signal 15 delivered to analysis arrangement 17. A particularly simple manner of determining the average energy is obtained when temperature controller 14 is configured as a two-position temperature controller. Corresponding signal profiles are shown in FIGS. 2 and 3.

Figure 2:
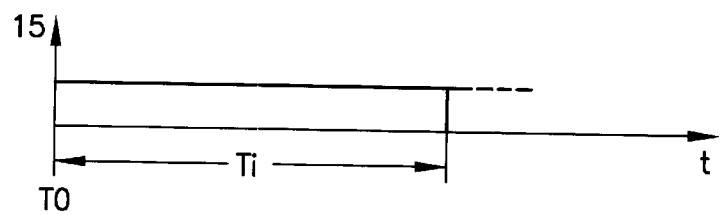
FIG. 2 shows a heating signal as a function of time, beginning at a starting time at least during an observation time interval.
Figure 3:
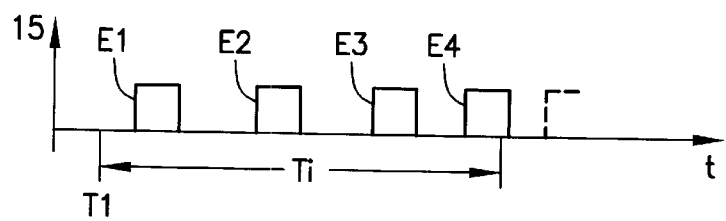
FIG. 3 shows the heating signal, including switch-on events, as the function of time, beginning at an operating time at least during the observation time interval.

FIG. 2 shows the operating situation beginning with starting time T0. After heating signal 15 occurs at starting time T0, in the case of the component 10 that has cooled off, heating signal 15 is present during the entire observation time interval Ti. The average energy delivered to resistance heating element 12 can be obtained by integrating heating signal 15. With a two-position temperature controller, integration becomes simply summing the switched-on times. Threshold S is to be defined in this case as a maximum time for the switched-on duration during observation time interval Ti. In the exemplary embodiment shown in FIG. 2, the switched-on time exceeds threshold S that is to be defined, so that operational readiness signal B does not occur.

Operational readiness signal B can be issued only when the average energy delivered to resistance heating element 12 falls below threshold S. One such case is shown in FIG. 3. A two-position temperature controller is again assumed to be present. Beginning from an arbitrary operating time T1, the average energy delivered to resistance heating element 12 during observation time interval Ti is once again determined. The energy determination is once again limited to summing the switched-on times exhibited by heating signal 15 as shown in FIG. 3. In the exemplary embodiment shown, four switch-on events E1, E2, E3, E4 occur in observation time interval Ti. The sum of the switched-on durations is compared to threshold S. If the sum of the switched-on durations within observation time interval Ti falls below threshold S, operational readiness signal B is issued.

Another advantageous embodiment provides for analyzing the number of switch-on events E1, E2, E3, E4 that occur during observation time interval Ti. In the operating situation shown in FIG. 2, only one switch-on event is present in observation time interval Ti. At the later operating time T1 shown in FIG. 3, four switch-on events E1, E2, E3, E4 occur during observation time interval Ti. If the number of switch-on events E1, E2, E3, E4 exceeds a predefined number, for example the number 3, operational readiness signal B is then issued.

Threshold S, which corresponds to the average energy delivered to resistance heating element 12 in observation time interval Ti, is preferably determined experimentally. Based on an experiment in which component 10 to be heated has reached the predefined operating temperature, it is possible to ascertain the average energy necessary to maintain the operating temperature. The threshold can then be defined as a total quantity of energy which must fall below a certain value during one observation time interval Ti in order for operational readiness signal B to be issued. According to the exemplary embodiments, according to the present invention threshold S can constitute a maximum time which must not be exceeded, or can be a minimum number of switch-on events E1, E2, E3, E4 which must be exceeded within one observation time interval Ti.

What is claimed is:

1. A circuit for heating a component and generating an operational readiness signal when the component reaches a predefined operational temperature, comprising:
   a resistance heating element thermally coupled to the component, the heating element having an actual temperature;
   an electrical energy source for powering the resistance heating element;
   a temperature controller for regulating the actual temperature of the resistance heating element by controlling an amount of energy supplied to the resistance heating element by the energy source, the controller producing a heating signal as a function of at least the actual temperature of the resistance heating element and the predefined operational temperature; and
   an analysis device configured to determine an average amount of energy delivered to the resistance heating element over at least one observation time interval and to generate the operational readiness signal in accordance with the average amount of energy delivered to the resistance heating element over the at least one observation time interval being below a predefined threshold.

2. The circuit according to claim 1, wherein the operational readiness signal is generated as a function of the predefined threshold and an integration sum, the integration sum being produced by integrating the heating signal over at least the one observation time interval.

3. The circuit according to claim 1, wherein the temperature controller includes a two-position controller, the two-position controller being capable of connecting occasionally the resistance heating element to the electrical energy source, whereby the amount of energy supplied to the resistance heating element by the energy source is controlled.

4. The circuit according to claim 3, wherein the predefined threshold is defined as a duration, the operational readiness signal being generated as a function of the duration and a switch-on time of the heating signal.

5. The circuit according to claim 3, wherein the predefined threshold is defined as a number of occurrences, the operational readiness signal being generated as a function of the number of occurrences and a number of switch-on events of the heating signal.

6. The circuit according to claim 1, wherein the temperature controller determines the actual temperature of the heating element as a function of an internal resistance of the resistance heating element.

7. The circuit according to claim 2, wherein the temperature controller determines the actual temperature of the heating element as a function of an internal resistance of the resistance heating element.

8. A gas sensing device capable of generating an operational readiness signal when the device is in an operational state, comprising:
   at least one gas sensor having a predefined operational temperature;
   a resistance heating element thermally coupled to at least the one gas sensor, the heating element having an actual temperature;
   an electrical energy source for powering the resistance heating element;
   a temperature controller for regulating the actual temperature of the resistance heating element by controlling an amount of energy supplied to the resistance heating element by the energy source, the controller producing a heating signal as a function of at least the actual temperature of the resistance heating element and the predefined operational temperature; and
   an analysis device configured to determine an average amount of energy delivered to the resistance heating element over at least one observation time interval and to generate the operational readiness signal in accordance with the average amount of energy delivered to the resistance heating element over the at least one observation time interval being below a predefined threshold.

9. The circuit according to claim 8, wherein the at least one gas sensor detects at least one constituent of inhaled air.

10. The circuit according to claim 8, wherein the at least one gas sensor detects at least one constituent of an exhaust gas of an internal combustion engine.

11. A circuit for heating a component, comprising:
    a resistance heating element thermally coupled to the component;
    an electrical energy source configured to power the resistance heating element;
    a temperature controller configured to regulate a temperature of the resistance heating element as a function of an actual temperature of the resistance heating element and a predefined reference temperature; and
    an analysis device configured to determine an average energy delivered to the resistance heating element in at least one observation time interval, to determine whether the average energy is below a predefined threshold and to determine that a temperature of the component has at least approximately reached a predefined operating temperature when the average energy is below the predefined threshold.

12. The circuit according to claim 11, wherein the temperature controller includes a two-position controller configured to occasionally connect the resistance heating element to the energy source.

13. The circuit according to claim 12, wherein the threshold is defined as a duration not to be exceeded within the observation time interval in accordance with a switch-on duration of a heating signal emitted by the two-position controller.

14. The circuit according to claim 12, wherein the threshold is defined as a number of switch-on events that must be exceeded during the observation time interval.

15. The circuit according to claim 11, wherein the resistance heating element is configured so that an internal resistance of the resistance heating element is indicative of its temperature.

16. The circuit according to claim 11, wherein the component includes at least one gas sensor.

17. The circuit according to claim 16, wherein the gas sensor is configured to detect at least one component of inhaled air.

18. The circuit according to claim 16, wherein the gas sensor is configured to detect at least one component of an internal combustion engine exhaust gas.

* * * * *

UNITED STATES PATENT AND TRADEMARK OFFICE
CERTIFICATE OF CORRECTION

PATENT NO.     : 6,429,410 B1
DATED          : August 6, 2002
INVENTOR(S)    : Stefan Koch It is certified that error appears in the above-identified patent and that said Letters Patent is hereby corrected as shown below:

Column 1,
Lines 50 and 51, delete the first sentence "A temperature of the component to be heated is not necessary" and insert -- A circuit according to the present invention has an advantage that direct or indirect sensing of the temperature of the component to be heated is not necessary --.

Signed and Sealed this

Sixteenth Day of September, 2003

JAMES E. ROGAN
*Director of the United States Patent and Trademark Office*